United States Patent [19]

Collington et al.

[11] Patent Number: 4,977,163

[45] Date of Patent: Dec. 11, 1990

[54] AMINOCYCLOPENTANOL ACIDS AND ESTERS AND THEIR PREPARATION AND PHARMACEUTICAL FORMULATION

[75] Inventors: Eric W. Collington, Welwyn; Peter Hallett, Royston; Christopher J. Wallis, Royston; Alan Wadsworth, Royston; Norman F. Hayes, Hitchin, all of England

[73] Assignee: Glaxo Group Limited, London, England

[21] Appl. No.: 183,293

[22] Filed: Apr. 11, 1988

Related U.S. Application Data

[63] Continuation of Ser. No. 750,655, Jul. 1, 1985, abandoned, which is a continuation of Ser. No. 584,300, Mar. 5, 1984, abandoned, which is a continuation of Ser. No. 437,332, Oct. 28, 1982, abandoned, which is a continuation-in-part of Ser. No. 372,823, Apr. 28, 1982, abandoned.

[30] Foreign Application Priority Data

Apr. 29, 1981 [GB] United Kingdom ............... 8113238
Jul. 2, 1981 [GB] United Kingdom ............... 8120459

[51] Int. Cl.$^5$ .............. A61K 31/445; A61K 31/535; C07D 211/14; C07D 295/112
[52] U.S. Cl. ................. 514/317; 514/227.5; 514/239.5; 544/58.1; 544/171; 546/238; 546/239
[58] Field of Search ............. 260/293, 243.3, 244.4, 260/330.3, 330.6; 514/211, 212, 222, 227.5, 230, 233, 236, 239.5, 255, 315, 316, 317, 319, 326, 422, 429; 540/596, 610; 544/58.1, 58.2, 58.6, 58.7, 88, 101, 107, 121, 146, 171, 357, 360, 389, 399; 546/187, 191, 205, 206, 213, 238, 239; 548/527, 573

[56] References Cited

U.S. PATENT DOCUMENTS

| | | | |
|---|---|---|---|
| 4,182,903 | 1/1980 | Favara et al. | 562/503 |
| 4,189,606 | 2/1980 | Favara et al. | 562/455 |
| 4,239,778 | 12/1980 | Venton et al. | 424/305 |
| 4,265,891 | 5/1981 | Collington et al. | 544/58.1 |
| 4,327,092 | 4/1982 | Collington et al. | 424/246 |
| 4,342,756 | 8/1982 | Collington et al. | 546/205 |
| 4,371,530 | 2/1983 | Collington et al. | 424/244 |
| 4,409,213 | 10/1983 | Collington et al. | 544/58.6 |
| 4,410,521 | 11/1983 | Collington et al. | 424/244 |
| 4,438,111 | 3/1984 | Collington et al. | 544/141 |
| 4,438,112 | 3/1984 | Collington et al. | 424/244 |

FOREIGN PATENT DOCUMENTS 0044711 1/1982 European Pat. Off. .

OTHER PUBLICATIONS

Floyd et al., *Tetrahedron Letters*, No. 32, (1972), pp. 3269–3272.
Miller et al., *Prostaglandins*, 11, (1976), pp. 77–84.
Anderson et al., *Advances in Prostaglandins & Thromboxane Research*, vol. 1, pp. 271, 275, 283 and 288, (1976).
Corey et al., *Journal of Organic Chemistry*, vol. 37, (1972), pp. 3043–3044.
Dieter Orth et al., *Topics in Current Chemistry*, 72:51–97, (1977).
G. C. Le Breton et al., *Proc. Natl. Acad. Sci. U.S.A.*, 76:4097–4101, (1979).

*Primary Examiner*—Joseph Paul Brust
*Assistant Examiner*—Mary Sue Howard
*Attorney, Agent, or Firm*—Bacon & Thomas

[57] ABSTRACT

Compounds are described of the formula

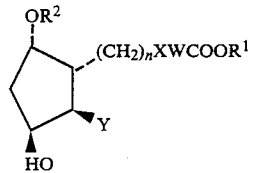

in which
$R^1$ is H, $C_{1-6}$ alkyl or $C_{7-10}$ aralkyl;
W is $C_{1-7}$ alkylene;
X is cis or trans —CH=CH— or —CH$_2$CH$_2$—;
n is 1 or 2;
Y is a saturated heterocyclic amino group having 5–8 ring members;
$R^2$ is (i) substituted or unsubstituted phenylalkyl, thienylalkyl or naphthylalkyl or (ii) substituted or unsubstituted cinnamyl; and their salts and solvates.

These compounds inhibit blood platelet aggregation and bronchoconstriction and may be formulated for use as antithrombotic and antiasthmatic agents.

13 Claims, No Drawings

AMINOCYCLOPENTANOL ACIDS AND ESTERS AND THEIR PREPARATION AND PHARMACEUTICAL FORMULATION

This is a continuation of application Ser. No. 750,655, filed Jul. 1, 1985, now abandoned, which is a continuation of application Ser. No. 584,300 filed Mar. 5, 1984, now abandoned, which in turn is a continuation of application Ser. No. 437,332, filed Oct. 28, 1982, now abandoned, which is a continuation-in-part of application Ser. No. 372,823, filed Apr. 28, 1982, now abandoned.

British Patent Specifications Nos. 2028805A, 2070591A and 2075503A referred to herein correspond to Collington et al U.S. Pat. No. 4,265,891 and Applications Nos. 23315, 223316 and 258721, which are incorporated herein by reference.

The endoperoxides prostaglandins $G_2$ and $H_2$ and thromboxane $A_2$ are naturally occurring reactive metabolites of arachidonic acid in human platelets. They are not only potent aggregatory agents but are also constrictors of vascular and bronchial smooth muscle, and therefore substances which antagonise their effects are of considerable interest in human medicine.

We have now found a new group of compounds which have shown endoperoxide and thromboxane antagonist activity, and are therefore of interest in the treatment of asthma and cardiovascular diseases.

This group of compounds has the general formula (I)

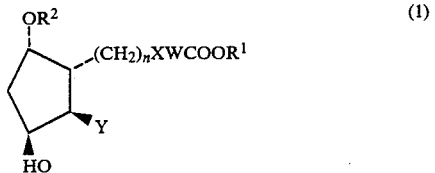

(1)

wherein $R^1$ is a hydrogen atom, $C_{1-6}$ alkyl or $C_{7-10}$ aralkyl;
W is straight or branched $C_{1-7}$ alkylene;
X is cis or trans —CH=CH— or —CH$_2$CH$_2$—;
n is 1 or 2;
Y is a saturated heterocyclic amino group (attached to the cyclopentane ring via the nitrogen atom) which has 5-8 ring members and (a) optionally contains in the ring —O—, —S—, —SO$_2$—, or —NR$^3$ (where $R^3$ is a hydrogen atom, $C_{1-7}$ alkyl or aralkyl having a $C_{1-4}$ alkyl portion); and/or (b) is optionally substituted by one or more $C_{1-4}$ alkyl groups; and $R^2$ is (i) straight or branched $C_{1-5}$ alkyl substituted by (a) phenyl [optionally substituted by $C_{1-6}$ alkyl, $C_{5-7}$ cycloalkyl, phenylalkyl having a $C_{1-3}$ alkyl portion, thienyl, phenyl (optionally substituted by $C_{1-4}$ alkyl, $C_{1-4}$ alkoxy or phenyl), benzoyl (optionally substituted by $C_{1-4}$ alkyl, $C_{1-4}$ alkoxy, halogen, trifluoromethyl or phenyl) or $C_{5-7}$ cycloalkanoyl], (b) thienyl [optionally substituted by $C_{1-6}$ alkyl, $C_{1-6}$ alkoxy, $C_{5-7}$ cycloalkyl or phenyl (optionally substituted by $C_{1-3}$ alkyl, $C_{1-3}$ alkoxy or halogen)], or (c) naphthyl (optionally substituted by $C_{1-4}$ alkyl or $C_{1-4}$ alkoxy), or (ii) cinnamyl (optionally substituted by benzoyl); including the physiologically acceptable salts and solvates (e.g. hydrates) thereof.

The structural formulae herein are to be understood to include the enantiomers of each of the compounds concerned as well as mixtures of the enantiomers including racemates, even though the precise structure as set out only relates to one enantiomer.

The amino group Y enables the compounds to form salts with inorganic or organic acids, e.g. hydrochlorides or maleates. Also, when $R^1$ represents a hydrogen atom salts may be formed with bases. Examples of such salts are alkali metal (e.g. sodium or potassium), alkaline earth metal ( e.g. calcium or magnesium), ammonium, substituted ammonium (e.g tromethamine or dimethylaminoethanol), piperazine, N,N-dimethylpiperazine, morpholine, piperidine and tertiary amino (e.g. trimethylamine) salts.

The heterocyclic amino group Y may for example have a 5,6 or 7-membered ring, e.g. pyrrolidino, piperidino, morpholino, piperazino, thiamorpholino, 1,1-dioxothiamorpholino homomorpholino and hexamethyleneimino. Examples of the optional substituents ($R^3$) which may be present on a second nitrogen atom in the ring are methyl, ethyl, butyl, hexyl, benzyl, and phenethyl. The carbon atoms of the heterocyclic rings may for example be substituted by methyl, ethyl or butyl. Y is preferably a morpholino or piperidino group.

When $R^2$ is a substituted alkyl group, the alkylene portion may for example contain 1-3 carbon atoms (e.g. methylene, ethylene or propylene) and is preferably a methylene group.

In $R^2$ groups of the type (i) (a), the phenyl group may be substituted by, for example, methyl, ethyl, t-butyl, cyclohexyl, benzyl, phenethyl, phenyl (optionally substituted by methyl, ethyl, methoxy or butoxy), benzoyl (optionally substituted by methyl, ethyl, methoxy, butoxy, chlorine or bromine) or cyclohexanoyl groups.

In $R^2$ groups of the type (i) (b), the thienyl group may be substituted by, for example methyl, ethyl, methoxy, ethoxy, cyclohexyl or phenyl (optionally substituted by methyl, ethyl, methoxy, ethoxy, chlorine or bromine) groups.

$R^2$ is preferably a benzyl group in which the phenyl group is substituted by thienyl or phenyl (which phenyl group itself may be optionally substituted by $C_{1-4}$ alkyl or $C_{1-4}$ alkoxy); or cinnamyl.

Particularly preferred $R^2$ groups are benzyl groups in which the phenyl portion is substituted (preferably in the para-position) by a phenyl, tolyl or methoxyphenyl group.

In the group —(CH$_2$)$_n$XWCOOR$^1$, n is preferably 2 and X is preferably cis —CH=CH—.

W may for example contain 1-5 carbon atoms in a straight or branched chain, and is preferably —CH$_2$CH$_2$CH$_2$— when n is 1 and —CH$_2$CH$_2$— when n is 2.

Examples of suitable $R^1$ groups are $C_{1-3}$ alkyl (e.g. methyl), benzyl and phenethyl; however, $R^1$ is preferably a hydrogen atom.

Thus a particularly preferred group of compounds has the formula (1) in which:

n is 1 and W is —CH$_2$CH$_2$CH$_2$— or n is 2 and W is —CH$_2$CH$_2$—, X is cis —CH=CH—, $R^1$ is a hydrogen atom, Y is morpholino or piperidino, and $R^2$ is benzyl in which the phenyl group is substituted by phenyl, tolyl or methoxyphenyl, and the physiologically acceptable salts and solvates thereof.

Important compounds of this type are [1α(Z), 2β, 3β, 5α]-(+)-7-[5-[[(1,1'-biphenyl)-4-yl]methoxy]-3-hydroxy-2-(4-morpholinyl)cyclopentyl]-4-heptenoic acid and its 1R-isomer; [1o(Z), 2β, 3β, 5o]-(+)-7-[5-[[(1,1'- biphenyl)-4-yl]methoxy]-3-hydroxy-2-(1-piperidinyl)-cyclopentyl]-4-heptenoic acid and its 1R-isomer; and the physiologically acceptable salts and solvates (e.g. hydrates) thereof. The 1R-isomers of these compounds are particularly important, especially the hydrochloride salt of the 1R-isomer of the just-mentioned piperidinyl compound.

In general, the compounds of formula (1) in which the carbon atom carrying the —$(CH_2)_nXWCOOR^1$ group is in the R-configuration (and mixtures containing this isomer) are preferred.

Compounds of formula (1) inhibit blood platelet aggregation and bronchoconstriction. To determine inhibition of blood platelet aggregation, starved guinea pigs are dosed orally with the compound to be tested in a suitable vehicle. Platelet rich plasma is prepared from each animal and aggregation to a range of collagen concentrations is measured after the method of Born (Nature 194, 927–929, (1962)). Collagen concentration-effect curves for each sample of plasma are calculated and results are expressed as the shift of the curves following treatment with the compound.

The ability of the compounds of the invention to inhibit bronchoconstriction is determined either in the anaesthetized guinea pig by measuring the effect of the compound to be tested on the dose response curve of the bronchoconstrictor [1R-[1α,4α, 5β(Z), 6α(1E, 3S*)]]-7-[6-(3-hydroxy-1-octenyl)-2-oxabicyclo [2,2,1] hept-5-yl]-5-heptenoic acid (U-46619) or by the test described by K. M. Lulich et al in British Journal of Pharmacology 58, 71–79 (1976) except guinea pig lung is used instead of cat lung.

The compounds are thus of interest in the treatment of asthma, and as inhibitors of platelet aggregation and thrombosis for use in renal dialysis and the treatment and prevention of occlusive vascular diseases such as arteriosclerosis, atherosclerosis, peripheral vascular disease, cerebral vascular disease including transient ischaemic attacks, stroke, pulmonary embolism, diabetic retinopathy, post operative thrombosis, angina and myocardial infarction. They may be formulated in conventional manner for use, with one or more pharmaceutical carriers.

For oral administration, the pharmaceutical composition may take the form of, for example, tablets, capsules, powders, solutions, syrups, or suspensions prepared by conventional means with acceptable excipients.

The compounds may be formulated for parenteral administration by bolus injections or continuous infusion. Formulations for injections may be presented in unit dosage form in ampoules, or in multi-dose containers, with an added preservative. The compositions may take such forms as suspensions, solutions or emulsions in oily or aqueous vehicles, and may contain formulatory agents such as suspending, stabilising and/or dispersing agents. Alternatively, the active ingredient may be in powder form for reconstitution before use with a suitable vehicle, e.g. sterile pyrogen-free water.

For administration by inhalation the compounds are conveniently delivered in the form of an aerosol spray presentation from pressurised packs or a nebuliser, or as a cartridge from which the powdered composition may be inhaled with the aid of a suitable device. In the case of a pressurised aerosol the dosage unit may be determined by providing a valve to deliver a metered amount.

For use as antithrombotic agents, the compounds are preferably administered orally, for example in amounts of 0.05 to 10 mg/kg body weight, 1 to 4 times daily.

For use in the treatment of asthma, the compounds may also be administered orally in amounts of 0.05 to 10 mg/kg body weight, 1 to 4 times daily; preferably however they are administered by inhalation at doses varying from 0.3 to 30 mg, 1 to 4 times daily. The compounds may be used in combination with other antiasthmatic agents.

The precise dose administered will of course depend on the age and condition of the patient.

Suitable methods for preparing compounds of formula (1) are described below. The R groups and n, W, X and Y are as defined above except where otherwise indicated.

(a) Compounds of formula (1) may be prepared by reducing a compound of formula (2)

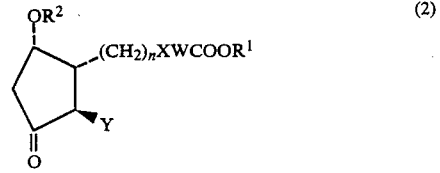

The reduction may for example be effected with a selective reducing agent such as diisobutylaluminium-2, 6-di-t-butyl-4-methylphenoxide, lithium trisiamylborohydride, 2,6-di-tert-butyl-4-methylphenoxymagnesium hydride or potassium tri-isopropoxyborohydride, or (when $R^1$ is a hydrogen atom) lithium tri-sec-butyl borohydride. The reaction temperature may be from $-10°$ to $-78°$ C. Tetrahydrofuran and toluene are suitable solvents.

Where a carbonyl group is present in $R^2$, this will need to be in a protected state during this reaction. Conventional protection methods may be used, with regard to the reducing conditions.

Many of the intermediates of formula (2) are described in UK Patent Specifications Nos. 2028805A, 2070591A and 2075503A. Other compounds of formula (2) may be prepared by the general methods described in those specifications, using starting materials containing the desired $R^2$ group.

(b) Compounds in which $R^1$ is a hydrogen atom may be prepared by hydrolysing a corresponding ester (e.g. a $C_{1-6}$ alkyl ester), e.g. using a base such as NaOH or KOH in a suitable solvent (e.g. methanol) at room temperature to 50° C.

(c) Compounds in which R is $C_{1-6}$ alkyl or $C_{7-10}$ aralkyl may be prepared by esterification of the corresponding carboxylic acid. Conventional esterification techniques may be used, for example by reaction with an appropriate alcohol in the presence of a mineral acid such as hydrochloric acid or sulphuric acid.

Alternatively, the acid may be converted into an activated derivative (e.g. a corresponding mixed anhydride) e.g. by reaction with an alkyl chloroformate (e.g. isobutyl chloroformate) in the presence of a suitable base, e.g. triethylamine or pyridine. The activated derivative can then be reacted with an appropriate alcohol, for example using a solvent such as acetone and a temperature of $-10°$ C. to room temperature. (d) Compounds of formula (1) in which X is —$CH_2CH_2$— may be prepared by catalytic hydrogenation of a corresponding compound in which X is —CH=CH—, using a catalyst such as palladium oxide. Alcohols such as ethanol are suitable solvents and the reaction may be performed at room temperature.

(e) Compounds of formula (1) may also be prepared by reduction of a corresponding compound of formula (1) in which X is an acetylene group. Suitable methods of reduction include using hydrogen in the presence of a catalyst, e.g. palladium on a support (e.g. $CaCO_3$ or $BaSO_4$) and poisoned for example by lead or quinoline. Suitable solvents include ethyl acetate and methanol. This reaction is particularly suitable for preparing compounds in which X is cis —CH=CH—.

The acetylenes required as starting materials in which n is 2 may be prepared by selective reduction (e.g. by method (a) above) of the corresponding cyclopentanone. The latter compounds may be prepared by the methods generally described in British Patent Specification No. 2075503A.

Acetylenes in which n is 1 may be prepared by first brominating (e.g. with bromine in $CH_2Cl_2$) a compound of formula (3)

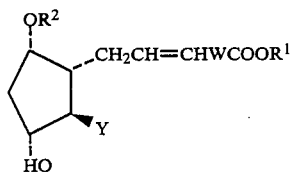

to give the corresponding compound in which X is —CHBr.CHBr—. The latter dibromo compound is then dehydrobrominated to form the acetylene group, for example in two stages, using potassium t-butoxide first at 0° C. and then at room temperature. Epimerisation of the α-hydroxy group (e.g. as described below) then gives the required starting material.

The starting materials of formula (3) may be prepared by the methods generally described in British Patent Specifications Nos. 2028805A and 2070591A.

(f) Compounds of formula (1) may also be prepared by epimerising the corresponding compound in which the ring hydroxy group is in the α-configuration, for example by the use of triphenylphosphine in the presence of an acid (such as benzoic acid) and $(C_2H_5OOC.N)_2$ at room temperature in a suitable solvent such as tetrahydrofuran, followed where necessary by treatment with a base such as NaOH.

The starting materials for this process may be prepared by the methods generally described in British Patent Specifications Nos. 2028805A, 2070591A and 2075503A.

(g) Compounds of formula (1) in which n is 2, X is cis —CH=CH— and $R^1$ is a hydrogen atom may be prepared by reacting a compound of formula (4)

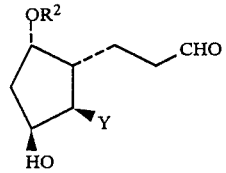

with an appropriate Wittig reagent, e.g. a phosporane of formula $R_3{}^4P$=CHWCOOH (where $R^4$ is $C_{1-6}$ alkyl or aryl, e.g. monocyclic aryl such as phenyl) or a salt thereof, e.g. the potassium salt. Suitable reaction solvents include hydrocarbons (e.g. benzene and toluene), ethers (e.g. tetrahydrofuran), dialkylsulphoxides (e.g. dimethylsulphoxide), alcohols and halogenated hydrocarbons. The reaction may be carried out at any suitable temperature from −70° to 50° C., preferably at room temperature.

The intermediates of formula (4) may be prepared from compounds of formula (5)

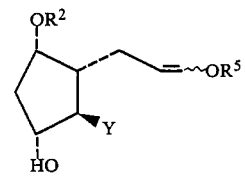

(where $R^5$ is $C_{1-4}$ alkyl) by oxidation of the hydroxy group followed by selective reduction (e.g. by process (a) above) of the so-formed oxo group. The compounds of formula (5) may be prepared by the methods generally described in British Patent Specification No. 2075503A.

(h) Compounds of formula (1) in which $R^1$ is a hydrogen atom may be prepared by selective oxidation of the corresponding alcohol of formula (6)

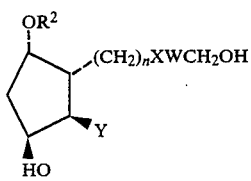

The oxidation may for example be effected with oxygen in the presence of a catalyst such as platinum dioxide in a suitable solvent (e.g. acetone) at an elevated temperature (e.g. 50° C).

The intermediates of formula (6) may be prepared by reducing a compound of formula (1), for example with $LiAlH_4$.

(i) Compounds of formula (1) in which X is trans —CH=CH— may be prepared by isomerising the corresponding cis compound. The isomerisation may for example be effected by treatment with p-toluene sulphinic acid in dioxan (e.g. at reflux) or azobisisobutyronitrile and thiophenol, using for example a hydrocarbon solvent (e.g. benzene) and any suitable temperature up to reflux.

(j) In the preparation of the compounds of formula (1), the ring hydroxy group will sometimes be protected and its liberation may be the final step in the synthesis. Conventional methods of protection may be used, and the protecting group may be removed by acid or alkaline hydrolysis depending on its nature. Protection in the form of the tetrahydropyranyloxy group is preferred; this may be removed by acid hydrolysis.

(k) Where salts of compounds of formula (1) are desired such salts may be formed by conventional methods, for example by treating acids of formula (1) with appropriate bases. Salts may also be formed with acids. For example, amine salts are conveniently prepared by adding the amine to a solution of an acid of formula (1) in a solvent such as ether. Salts of inorganic bases may be prepared by adding the base to a solution of the acid in an aqueous organic solvent. Certain salts may also be prepared by exchange of cation; for example, calcium salts may be prepared by addition of a calcium salt (e.g. the chloride or acetate) to a solution of a salt of a compound of formula (1), e.g. an amine or alkali metal salt.

Salts of acids may be prepared by adding the acid (e.g. hydrogen chloride) to a solution of the compound of formula (1) in an organic solvent such as ether.

When a specific enantiomer of formula (1) is required, starting materials having the desired sterochemical configuration should be used in the above processes. Such intermediates may for example be prepared starting from an enantiomeric bromohydrin as generally described in British Patent Specification No. 2075503A.

The following examples illustrate the invention.
Temperatures are in °C.
The following abbreviations are used:
T.L.C. - Thin layer chromatography using $SiO_2$;
ER - ether;
EA - ethyl acetate;
THF - tetrahydrofuran;
DIBAL - diisobutylaluminium hydride;
DMSO - dimethylsulphoxide;
DMF - dimethylformamide.
PE - petroleum ether (b p. 60°–80°)
Chromatography was carried out using silica gel.
'Dried' refers to drying with $MgSO_4$.
'Hyflo' is a filtration aid.

The preparation of the following intermediates is described in British Patent Specification No. 2028805A;

INTERMEDIATE 1

[1α(Z),2β,5α]-(±)-7-[5-[((1,1'-Biphenyl)-4-yl]methoxy]-2-(4-morpholinyl)-3-oxocyclopentyl]-5-heptenoic acid.

INTERMEDIATE 2

[1α(Z),2β,5α]-(±)-Methyl 7-[5-(4-Cyclohexylphenylmethoxy)-2-(4-morpholinyl)-3-oxocyclopentyl]-5-heptenoate

INTERMEDIATE 3

[1α(Z),2β,3α,5α]-(±)-Methyl 7-[5-Hydroxy-2-(4-morpholinyl)-3-[(tetrahydro-2H-pyran-2-yl)oxy]cyclopentyl]-5-heptenoate The preparation of the following intermediates is described in British Patent Specification No. 2070591A:

INTERMEDIATE 4

[1α(Z),2β,5α]-(±)+-7-[5-[[4'-Methoxy(1,1'-biphenyl)-4-yl]methoxy]-2-(4-morpholinyl)-3-oxocyclopentyl]-5-heptenoic acid.

INTERMEDIATE 5

[1α(Z),2β,5α]-(±)-7-[5-[[4'-Methyl(1,1'-biphenyl)-4-yl]methoxy]-2-(4-morpholinyl)-3-oxocyclopentyl]-5-heptenoic acid.

The preparation of the following intermediates is described in British Patent Specification No. 2075503A:

INTERMEDIATE 6

[1α(Z),2β,5α]-(±)+-7-[5-[[(1,1'-Biphenyl)-4-yl]methoxy]-2-(4-morpholinyl)-3-oxocyclopentyl]-4-heptenoic acid.

INTERMEDIATE 7

[1α(Z),2β,5α]-(±)+-7-[2-(4-Morpholinyl)-3-oxo-5-[(2-phenylthien-4-yl)methoxy]cyclopentyl]-4-heptenoic acid

INTERMEDIATE 8

[1α(Z),2β,5α]-(±)-9-[5-[[(1,1'-Biphenyl)-4-yl]methoxy]-2-(4-morpholinyl)-3-oxocyclopentyl]-6-nonenoic acid.

INTERMEDIATE 9

[1α(Z),2β,5α]-(±)-7-[2-(4-Morpholinyl)-3-oxo-5-[4-(phenylmethyl)phenylmethoxy]cyclopentyl]-4-heptenoic acid compound with piperazine (2:1).

INTERMEDIATE 10

[1α(Z),2β,5α]-(±)-7-[5-[[4'-Methoxy(1,1'-biphenyl)-4-yl]methoxy]-2-(4-morpholinyl)-3-oxocyclopentyl]-4-heptenoic acid.

INTERMEDIATE 11

[1α(Z),2β,5α]-(±)+-7-[5-[[4'-Methyl(1,1'-biphenyl)-4-yl]methoxy]-2-(4-morpholinyl)-3-oxocyclopentyl]-4-heptenoic acid.

INTERMEDIATE 12

[1α(Z),2β,5α]-(±)-7-[2-(4-Morpholinyl)-3-oxo-5-[4(thien-2-yl)phenoylmethoxy]cyclopentyl]-4-heptenoic acid, compound with piperazine (2:1).

INTERMEDIATE 13

[1α(Z), 2β,5α-(E)-(±)-7-[2-(4-Morpholinyl)-3-oxo-5-(3-phenyl-2-propenyl)oxy]cyclopentyl]-4-heptenoic acid.

INTERMEDIATE 14

[1α(Z),2β,5α-(±) -7-[5-[[(1,1'-Biphenyl)-4-yl]methoxy]-3-oxo-2-(4-thiomorpholinyl)cyclopentyl]-4-heptenoic acid

INTERMEDIATE 15

[1R-[1α(Z),2β,5α]]-(−)-7-[5-[[(1,1'-Biphenyl)-4-yl]methoxy]-2-(4-morpholinyl)-3-oxocyclopentyl]-4-heptenoic acid.

INTERMEDIATE 16

4-Bromomethyl-3'-methoxy(1,1'-biphenyl)

INTERMEDIATE 17

[1α(Z), 2β,3α,5α-(±) -Methyl 7-[[(1,1'-Biphenyl)-4-yl]methoxy]-3-hydroxy-2-(1-piperidinyl)cyclopentyl]-4-heptenoate.

INTERMEDIATE 18

[1α(Z),2β,3α,5α]-(±)-Methyl 7-[3-Hydroxy-5-[[3'-methoxy (1,1'-biphenyl)-4-yl]methoxy]-2-(4-morpholinyl)cyclopentyl]-5-heptenoate.

Sodium hydride (1.15 g, 46% dispersion in oil) was added to a stirred solution of Intermediates 3 (3 g) and 16 (6.1 g) in DMF (30 ml) under nitrogen and the mixture was stirred at 20° for 2.5 h. The mixture was poured into pH 6 phosphate buffer (200 ml) and extracted with $CH_2Cl_2$ (3×100 ml). The combined extracts were dried and evaporated to give an oil which was treated with 15:1 methanol - c.H$_2$SO$_4$ (70 ml) for 0.5 h, then poured into saturated NaHCO$_3$ solution (200 ml) and extracted with CH$_2$Cl$_2$ (3×100 ml). The combined extracts were dried and evaporated and the residue was purified by chromatography using 19:1 ER-methanol as eluent to give the title compound as an oil (1.59 g).

Analysis Found: C, 70.8; H, 8.0; N, 2.4; C$_{31}$H$_{41}$NO$_6$ requires: C, 71.1; H, 7.9; N, 2.7%.

INTERMEDIATE 19

[1α(Z),2β,5α]-(±)-Methyl 7-[5-[[3'-Methoxy(1,1'-biphenyl)-4-yl]methoxy]-2-(4-morpholinyl)-3-oxocyclopentyl]-5-heptenoate A solution of pyridine-sulphur trioxide complex (1.07 g) in dry DMSO (14 ml) was added dropwise to a cold (0°). stirred solution of Intermediate 18 (1.17 g) and triethylamine (1.85 ml) in CH$_2$Cl$_2$ (20 ml) under nitrogen. The mixture was stirred at 0° for 3 h then poured into pH 6 phosphate buffer (100 ml) and extracted with CH$_2$Cl$_2$ (3×50 ml). The combined extracts were dried and evaporated and the residue was purified by chromatography using ER as eluent to give the title compound as a solid (0.94 g). A portion recrystallised from ER-isopentane had m.p. 56°–59°.

INTERMEDIATE 20

[1α(Z),2β,5α-±]-Methyl 7-[5-[[(1,1'-Biphenyl)-4-[yl]methoxy]-3-oxo-2-(1-piperidinyl)cyclopentyl]-4-heptenoate A solution of pyridine-sulphur trioxide complex (0.76 g) in dry DMSO (6 ml) was added dropwise to a cold (0°), stirred solution of Intermediate 17 (0.59 g) and triethylamine (1.17 ml) in CH$_2$Cl$_2$ (6 ml). The mixture was stirred at 0° for 1 h then poured into pH 6 phosphate buffer (75 ml) and extracted with ether (2×50 ml). The combined extracts were dried and evaporated and the residue was purified by chromatography using 1:1 ER-PE as eluent to give the title compound as a solid (0.36 g) m.p. 55°–59°.

INTERMEDIATE 21

[1α(Z),2β,3β,5α]-(±)-Methyl 7-5-[[(1,1'-Biphenyl)-4-yl]methoxy]-2-[4-morpholinyl)-3-[(tetrahydro-2H-pyran-2-yl)oxy]cyclopentyl]-4-heptenoate, compound with ethyl acetate (8:1)

Dihydropyran (0.48 ml) was added dropwise to a cold (0°) solution of the compound of Example 5 (0.65 g) and anhydrous p-toluene sulphonic acid (0.34 g) in CH$_2$Cl$_2$ (15 ml). After 3 h, the solution was diluted with 8% NaHCO$_3$ solution (15 ml) and the layers were separated. The aqueous layer was washed with CH$_2$Cl$_2$ (15 ml) and the combined organic layers were dried and evaporated. The crude product was purified by chromatography using 1:1 EA-PE as eluent to give the title compound as an oil (0.65 g).

Analysis Found: C, 72.1; H, 8.4; N, 2.3%; C$_{35}$H$_{47}$NO$_6$ ⅓ (C$_4$H$_8$O$_2$) requires: C, 72.4; H, 8.2; N, 2.4.

INTERMEDIATE 22

[1α(Z),2β,3β,5α]-(±)-7-[5-[[(1,1'-Biphenyl)-4-yl]methoxy]-2-(4-morpholinyl)-3-[(tetrahydro-2H-pyran-2-yl)oxy]cyclopentyl]-4-heptenoic acid, compound with ethyl acetate (4:1)

A solution of Intermediate 21 (0.46 g) in methanol (5 ml) and 2N NaOH (1 ml) was stirred at 20° for 22 h. The solution was poured into water (10 ml) and extracted with ether (3×10 ml). The aqueous layer was added to pH 6 phosphate buffer (75 ml) and extracted with EA (3×25 ml). The combined EA extracts were dried and evaporated to give the title compound as a foam (0.41 g).

Analysis Found: C, 71.4; H, 8.2; N, 2.3; C$_{34}$H$_{45}$NO$_6$.¼ (C$_4$H$_8$O$_2$) requires: C, 71.8; H, 8.1; N, 2.4%.

INTERMEDIATE 23

[1α,2α,3β(Z),4β]-(±)-4-[[(1,1'-Biphenyl)-4-yl]methoxy]-3-(7-hydroxy-3-heptenyl)-2-(4-morpholinyl)cyclopentanol, compound with ethyl acetate (3:1)

A solution of the compound of Example 1a (0.8 g) in dry THF (25 ml) was added slowly to a stirred solution of lithium aluminium hydride (0.19 g) in dry THF (5 ml) under nitrogen. After 3 h, 1N NaOH (0.95 ml) was added followed by anhydrous magnesium sulphate 0.5 h later. The inorganic solids were removed and the filtrate was evaporated. The residue was purified by chromatography using 9:1 EA-methanol as eluent to give the title compound as an oil (0.575 g).

Analysis Found: C, 73.7; H, 8.6; N, 3.1; C$_{29}$H$_{34}$NO$_4$ ⅓ (C$_4$H$_8$O$_2$) requires: C, 73.6; H, 8.5; N, 2.8%.

The preparation of the following intermediates is described in British Patent Specification No. 2075503A:

INTERMEDIATE 24

(1α,2β,5α)-(±)-7-+[5-[[(1,1'-Biphenyl)-4-yl]methoxy]-2-(4-morpholinyl)-3-oxocyclopentyl]-4-heptynoic acid.

INTERMEDIATE 25

[1α(Z),2β,3α,5α]-(±)-Methyl 7-[5-[[(1,1'-Biphenyl)-4-yl]methoxy]-3-hydroxy-2-(4-morpholinyl)cyclopentyl]-4-heptenoate.

INTERMEDIATE 26

(1α,2β,3β,5α)-(±)-7-[5-[[(1,1'-Biphenyl)-4-yl]methoxy]-3-hydroxy-2-(4-morpholinyl)cyclopentyl]-4-heptynoic acid, compound with ethyl acetate (2:1)

from Intermediate 24, according to the procedure described in Example 1a Method 1. Purification by chromotography using 3:1 EA-methanol as eluent to give the title compound as a foam.

I.R. (CHBr$_3$) 3500–2300, 1725, 1675 cm$^{-1}$.

T.L.C. 1:20:79 Acetic acid-methanol-EA R$_f$0.15. The preparation of Intermediate 27 is described in British Patent Specification No. 2075503A.

INTERMEDIATE 27

[1R-(exo,endo)]-(−)-2-Bromo-3-hydroxybicyclo[3.2.0]heptan-6-one

INTERMEDIATE 28

[1R-(endo,anti)-(+)-5-Hydroxy-7-(1-piperidinyl)bicyclo-[2.2.1]heptan-2-one

A solution of Intermediate 27 (5.25 g) in acetone (50 ml) containing piperidine (6.3 ml) was stirred at 20° for 2.5 h in the dark. The mixture was poured into 8% NaHCO$_3$ solution (150 ml) and extracted with CH$_2$Cl$_2$ (3×100 ml). The combined extracts were dried and evaporated and the residue was purified by chromatography using ER as eluent. The title compound was obtained as a solid (4.7 g). A portion was recrystallised from ER-PE (b.p. 40°–60°) to give material of m.p. 87°–88°.

$[\alpha]_D^{25.5} = +68.7°$ (CHCl$_3$).

INTERMEDIATE 29

[1R-(endo,anti)]-(+)-5-[[(1,1'-Biphenyl)-4-yl]methoxy-7-(1-piperidinyl)bicyclo[2.2.1]heptan-2-one A mixture of Intermediate 28 (4.34 g) benzyltriethylammonium chloride (2 g) and biphenylmethyl bromide (6.7 g) in $CH_2Cl_2$ (100 ml) and 17N NaOH (60 ml) was stirred vigorously at 20° for 18 h. The phases were separated and the aqueous phase, diluted with water (100 ml), was extracted with $CH_2Cl_2$ (3×100 ml). The combined organic layers were washed with water (100 ml), dried and evaporated and the residue was purified by chromatography eluting with 4:1 PE (b.p. 40°-60°) -ER up to 1:1 PE (b.p. 40°-60°) -ER. The title compound was obtained as a solid 6.2 g). A portion was recrystallised from EA-PE to give material of m.p. 108°-110°.

$[\alpha]_D^{22} = +25.45°$ ($CHCl_3$).

INTERMEDIATE 30

[1R-(endo,anti)]-(−)6-[[(1,1'-Biphenyl)-4-yl]methoxy]-8-(1-piperidinyl)-2-oxabicyclo[3.2.1]octan-3-one Peracetic acid (13 ml; 6.12M) was added dropwise to stirred solution of Intermediate 29 (5.8 g) in $CH_2Cl_2$ (150 ml) at 20°. The mixture was stirred for 20 h, then diluted with water (250 ml). The phases were separated and the aqueous layer was extracted with $CH_2Cl_2$ (100 ml). The combined organic layers were added to a cold (0°) saturated solution of $Na_2SO_3$ (150 ml), then stirred vigorously at 20° for 1.5 h. The mixture was diluted with isopropyl acetate (200 ml) and the phases were separated. The aqueous layer was extracted with isopropyl acetate (2×100 ml) and the combined organic layers were washed with 0.5N NaOH (100 ml) and brine (150 ml), then dried and evaporated. The residue was purified by chromatography using 7:3 ER-PE (b.p. 40°-60°) as eluent to give a solid which was recrystallised from ER-PE to give the title compound as a colourless solid (2.3 g). m.p. 129.5°-130°

$[\alpha]_D^{22} = -26.5°$ ($CHCl_3$).

INTERMEDIATE 31

[1R-(1α,2β,3α,5α)]-5-[[(1,1'-Biphenyl)-4-yl]methoxy]-3-hydroxy-2-(1-piperidinyl)cyclopentane acetaldehyde A solution of Intermediate 30 (1.2 g) in dry $CH_2Cl_2$ (20 ml) was cooled (−78°) and stirred under nitrogen whilst a solution of DIBAL in hexane (5.25 ml; 1.43 M) was added dropwise. Methanol (20 ml) was added dropwise at −70° after 0.75 h and the cooling bath was removed. After stirring at 20° for 1 h, the precipitate was filtered off and washed well with methanol The combined filtrates were evaporated to give the title compound as a foam (1.2 g).

IR ($CHBr_3$) 3580, 3560, 2730, 1720 $cm^{-1}$.

INTERMEDIATE 32

[1R-(1α,2β,3α,4α)]-4-[[(1,1'-Biphenyl)-4-yl]methoxy]-3-(3-methoxy-2-propenyl)-2-(1-piperidinyl)cyclopentanol (Methoxymethyl)triphenylphosphonium chloride (3.8 g) was added over 10 min. to a cold (−5°) stirred solution of potassium tert-butoxide (1.27 g) in dry THF (35 ml). After 30 min., a solution of Intermediate 31 (1.18 g) in THF (15 ml) was added at 0° and stirring maintained for 30 min. The mixture was poured into 8% $NaHCO_3$ solution (150 ml) and extracted with EA (2×100 ml). The combined extracts were dried and evaporated and the residue was purified by chromatography using 4.1 EA-methanol as eluent to give the title compound as a semi-solid (0.9 g).

IR ($CHBr_3$) 3580, 3500, 1650 $cm^1$.

INTERMEDIATE 33

[2R-(2α,3β,4β)]-4-[[(1,1'-Biphenyl)-4-yl]methoxy]-3-[3-methoxy-2-propenyl)-2-(1-piperidinyl)cyclopentanone A solution of Intermediate 32 (0.84 g) in $CH_2Cl_2$ (8 ml) was cooled (5°) whilst triethylamine (1.95 ml) followed by pyridine-sulphur trioxide complex (1.27 g) in DMSO (8 ml) were added. After 1 h at 5° the mixture was poured into pH 6 phosphate buffer (100 ml) and extracted with ER (2×75 ml). The combined extracts were washed with water (50 ml) dried and evaporated and the residue was purified by chromatography using 1:1 ER-PE as eluent to give the title compound as an oil (0.725 g).

IR ($CHBr_3$) 1735, 1656 $cm^{-1}$.

INTERMEDIATE 34

[1R-(1α,2β,3β,5α)]-(+)-5-[[(1,1'-Biphenyl)-4-yl]methoxy]-3-hydroxy-2-(1-piperidinyl)cyclopentanepropanal A stirred solution of Intermediate 33 (0.69 g) in THF (15 ml) was cooled (−10°) whilst lithium tri-sec-butylborohydride in THF (5 ml; 1M) was added. After 1 h at −10°, 2N HCl (20 ml) was added, cautiously at first, and the mixture was stirred at 20° for 2 h. The mixture was washed with ether (50 ml) and then adjusted to pH 9 with 2N $Na_2CO_3$ and extracted with EA (4×50 ml). The combined extracts were dried and evaporated and the residue was purified by chromatography using 1:2 methanol - EA as eluent to give the title compound as a foam (0.206 g).

$[\alpha]_D^{23} = +54.90°$ ($CHCl_3$).

T.L.C. 15:7 EA-methanol $R_f$O13.

The preparation of Intermediate 35 is described in British Patent Specification No. 2075503A.

INTERMEDIATE 35

(endo,anti)-(+)-±-Hydroxy-7-(1-piperidinyl)bicyclo2.2.1]heptan-2-one, hydrochloride.

INTERMEDIATE 36

(endo,anti)-(±)-5-[[4'Methoxy(1,1'-biphenyl)-4-yl]methoxy]-7-(1-piperidinyl)bicyclo[2.2.1.]heptan-2-one A mixture of Intermediate 35 (6.64 g), benzyltriethylammonium chloride (2 g) and 4-(bromomethyl)-4'-methoxy(1,1'-biphenyl) (9.73 g) in $CH_2Cl_2$ (100 ml) and 17N NaOH (70 ml) was vigorously stirred at 20° for 16 h. The mixture was poured into water (140 ml), the phases separated and the aqueous layer was extracted with $CH_2Cl_2$ (100 ml). The combined organic layers were dried and evaporated and the residue was triturated with PE (50 ml) to give a solid which was recrystallised from 5:2 EA-PE to give the title compound as a solid (6.63 g) m.p. 112°-115°.

INTERMEDIATE 37

(endo,anti)-(±)-6-[[4'-Methoxy(1,1'biphenyl)-4-yl]methoxyl]-8-(1-piperidinyl)-2-oxobicyclo[3.2.1octan-3-one Peracetic acid (11.2 ml; 6.12M) was added slowly to a cooled (5°) stirred solution of Intermediate 36 (6.1 g) in $CH_2Cl_2$ (25 ml). The mixture was stirred at 20° for 64 h then added slowly to a cooled (5°) stirred mixture of saturated Na$_2$SO$_3$ (70 ml) and water (30 ml). After 1 h, isopropyl acetate (50 ml) was added and the layers were separated. The aqueous layer was extracted with isopropyl acetate (2×50 ml) and the combined organic layers were washed with 1N NaOH (100 ml) dried and evaporated. The residue was purified by chromatography using 1:1 EA-PE as eluent to give an oil which was triturated with ether to give the title compound as a solid (2 g) m.p. 105°–106°.

INTERMEDIATE 38

(1α,2β,3α,5α)-(±)-3-Hydroxy-5-[[4'-methoxy(1,1'-biphenyl)-4-yl]methoxy]-2-(1-piperidinyl)cyclopentane acetaldehyde DIBAL in hexane (7.9 ml; 1.43M) was added over 0.5 h to a cold (−70°), stirred solution of Intermediate 37 (1.9 g) in CH$_2$Cl$_2$ (15 ml). After 1.5 h methanol (15 ml) was added dropwise and the mixture was stirred at 20° for 2 h. The precipitate was filtered off and the solid was washed with methanol. The combined filtrates were evaporated and the residue was dissolved in CH$_2$Cl$_2$ (50 ml), dried and the solvent was removed to give the title compound as a foam (1.89 g).

IR (CHBr$_3$) 3580, 3535, 2730, 1710 cm$^{-1}$.

INTERMEDIATE 39

(1α,2β,3α,4α)-(±)-4-[[4'-Methoxy(1,1'-biphenyl)-4-yl]methoxy]-3-(3-methoxy-2-propenyl)-2-(1-piperidinyl)cyclopentanol (Methoxymethyl)triphenylphosphonium chloride (6.17 g) was added over 10 min. to a cold (0°) solution of potassium tert-butoxide (2.02 g) in dry THF (35 ml). After 15 min., a solution of Intermediate 38 (1.86 g) in THF (10 ml) was added dropwise and stirring was maintained for 1.5 h. The mixture was poured into pH 6 phosphate buffer (100 ml) and extracted with EA (2×50 ml). The combined extracts were dried and evaporated and the residue was purified by chromatography using 4:1 EA-methanol as eluent to give the title compound as a semi-solid (1.29 g).

IR (CHBr$_3$) 3520, 3330, 1653 cm$^{-1}$.

INTERMEDIATE 40

(2α,3β,4β)-(±)-4[[4'-Methoxy(1,1'-biphenyl)-4-yl]methoxy]-(3-(3-methoxy-2-propenyl)-2-(1-piperidinyl)cyclopentanone A solution of Intermediate 39 (0.4 g) in CH$_2$Cl$_2$ (4 ml) was cooled (0°) whilst triethylamine (0.95 ml) followed by pyridine-sulphur trioxide complex (0.65 g) in DMSO (4 ml) were added. After 1 h at 0° the mixture was poured into pH 6.5 phosphate buffer (50 ml) and extracted with ER (2×50 ml). The combined extracts were washed with brine (2×25 ml) dried and evaporated and the residue was purified by chromatography using 1:1 ER-PE (b.p. 40°–60°) as eluent to give the title compound as an oil.

IR (Neat) 1740, 1655 cm$^{-1}$.

INTERMEDIATE 41

[1α,2β,3β,5α]-(±)-3-Hydroxy-5-[[4'-methoxy(1,1'-biphenyl)-4-yl]methoxy]-2-(1-piperidinyl)cyclopentanepropanal DIBAL (1.43M in hexane, 14 ml) was added over 10 min. under nitrogen to an ice cooled solution of 2,6-di-t-butyl-p-cresol (8.8 g) in dry toluene (100 ml). After 1 h, the solution was cooled to −45° and a solution of Intermediate 40 (0.62 g) in toluene (20 ml) was added over 3 min. The temperature was allowed to rise to −10° over 1 h, then 2N HCl (40 ml) was added and the mixture stirred at room temperature for 1.5 h. The mixture was diluted with ER (100 ml) and the organic layer extracted with 1N H$_2$SO$_4$ (30 ml). The combined aqueous solutions were washed with ER (100 ml), basified with solid NaHCO$_3$ and the product extracted into CH$_2$Cl$_2$ (3×80 ml). The combined extracts were dried (Na$_2$SO$_4$) and concentrated, and the residue purified by chromatography using 2:1 EA-methanol as eluent to give the title compound as an oil (0.43 g).

IR (Neat) 3400(br.), 1720 cm$^{-1}$.

EXAMPLE 1

(a)

[1α(Z),2β,3β,5α]-(±)-7-[5-[[1,1'-Biphenyl)-4-yl]methoxy]-3-hydroxy-2-(4-morpholinyl)cyclopentyl]-4-heptenoic acid, compound with piperazine (2:1)

Method 1

A stirred solution of lithium tri-sec-butylborohydride in THF (12 ml, 1M) under nitrogen at −28° was treated slowly dropwise with a solution of Intermediate 6 (0.6 g) in dry THF (12 ml). After 3 h, the mixture was poured into 2N H$_2$SO$_4$ (20 ml) and pH 6.5 phosphate buffer (50 ml) and washed with ER (1×150 ml; 1×50 ml). The aqueous layer was adjusted to pH 6.5 with 2N NaOH and extracted with EA (2×100 ml).

The combined extracts were dried and evaporated and the residue was purified by chromatography using 4:1 EA-methanol as eluent to give a foam (0.47 g).

T.L.C. 1:20:79 Acetic acid-methanol-EA R$_f$ 0.17.

A portion of the foam (0.14 g) in ER-EA (4:1; 75 ml) was treated with a 0.1M solution of piperazine in ER-EA (4:1; 3 ml) and cooled to 5° to give the title compound as a solid (61 mg), m.p. 98°–100°.

Analysis Found: C, 71.1; H, 8.4; N, 5.2; C$_{29}$H$_{37}$NO$_5$.½(C$_4$H$_{10}$N$_2$) requires: C, 71.2; H, 8.1; N, 5.4%.

Method 2

A solution of Intermediate 22 (0.25 g) in acetone (5 ml) and 2N HCl (1 ml) was stirred at 20° for 4 h. The solution was poured into 8% NaHCO$_3$ solution (25 ml) and extracted with ether (3×10 ml). The aqueous layer was adjusted to pH 6 with 2N HCl (7 ml) and pH 6 phosphate buffer (25 ml) then was extracted with EA (3×20 ml). The combined EA extracts were dried and evaporated to give the title compound (acid) as a foam (0.176 g).

Method 3

A vigorously stirred mixture of Intermediate 23 (0.39 g) and pre-reduced Adams catalyst (0.5 g) in water (60 ml), acetone (30 ml) and 8% NaHCO$_3$ solution (18 ml) was heated at 50° for 9 h whilst oxygen was bubbled through. Fresh catalyst (0.5 g) in water (30 ml) was added and the oxygenated mixture was maintained at 50° for 11 h then 70° for 5 h. The catalyst was filtered off (hyflo) and the filtrate was adjusted to pH 10 with 2N NaOH. The solution was extracted with CH$_2$Cl$_2$ (4×50 ml) and then adjusted to pH 6 using 2N HCl and pH 6 phosphate buffer. The aqueous layer was extracted with CH$_2$Cl$_2$ (3×50 ml) and the extracts were dried and evaporated. The residue was purified by chromatography to give the title compound (acid) as a foam (0.031 g).

Method 4

A suspension of 5% Pd on CaCO$_3$ poisoned with lead (0.025 g) in EA (4 ml) containing quinoline (3 mg) was hydrogenated at 20° and atmospheric pressure for 1 h. A solution of Intermediate 26 (0.041 g) in EA (2 ml) was added and hydrogenation continued for 2.5 h. The catalyst was filtered off (hyflo) and the filtrate was evaporated. The residue in 0.5N NaOH (25 ml) was washed with EA (2×20 ml) then adjusted to pH 6 with 2N HCl. The aqueous layer was extracted with EA (2×25 ml) and the combined extracts were dried and evaporated to give the title compound (acid) as an oil (0.033 g).

Method 5

A solution of diethyl azodicarboxylate (0.293 g) in dry THF (5 ml) was added dropwise to a cold (0°), stirred solution of benzoic acid (0.195 g) triphenylphosphine (0.419 g) and Intermediate 25 (0.2 g) in dry THF (10 ml). The cooling bath was removed and the mixture was stirred at 20° for 1.5 h. The solvent was evaporated and the residue was purified by chromatography using initially 4:1 $CH_2Cl_2$ ER then 1:1 $CH_2Cl_2$ - acetone as eluent to give an oil. The oil was dissolved in methanol (5 ml) and 2N NaOH (1 ml) and kept at 20° for 18 h. The methanol was evaporated and the residue in 1N $H_2SO_4$ (3 ml) and water (10 ml) was washed with ether (3×20 ml). The aqueous layer was adjusted to pH 6.5 with 2N NaOH (0.5 ml) and pH 6.5 phosphate buffer (20 ml) then extracted with $CH_2Cl_2$ (3×20 ml). The combined extracts were dried and evaporated to give the title compound (acid) as a foam (0.051 g). The products of Methods 2–5 each had the following characteristics:

T.L.C. 1:20:79 acetic acid-methanol-ER Rf 0.17. I.R. ($CHBr_3$) 3500–2300 (v.broad), 1730, 1710 cm⁻. The following compounds were prepared by the procedure described for Method 1:

(b)
[1α(Z), 2β,3β,5α]-(±)-7-[5-[[(1,1'-Biphenyl)-4-yl]methoxy]-3-hydroxy-2-(4-morpholinyl)cyclopentyl]-5-heptenoic acid, compound with piperazine (2:1), from Intermediate 1. Purification of the acid by chromatography using 4:1 EA-methanol as eluent. The title compound (0.11 g) crystallised from a solution of the acid (0.105 g) and piperazine (0.020 g) in ER (32 ml) to give material of m.p. 121°–127°.

Analysis Found: C, 71.0; H, 8.2; N, 5.4; $C_{29}H_{37}NO_5.\frac{1}{2}(C_4H_{10}N_2)$ requires: C, 71.2; H, 8.1; N, 5.4%.

(c)
[1α(Z),2β,3β,5α]-(±)-7-[3-Hydroxy-5-[[4'-methoxy(1,1'-biphenyl)-4-yl]methoxy]-2-(4-morpholinyl)cyclopentyl]-5-heptenoic acid, compound with piperazine (2:1), m.p. 124°–132° from Intermediate 4.

Analysis Found: C, 69.4; H, 8.2; N, 5.2; $C_{30}H_{39}NO_6.\frac{1}{2}(C_4H_{10}N_2)$ requires: C, 69.5; H, 8.0; N, 5.1%.

(d)
[1α(Z),2β,3β,5α]-(±)-7-[3-Hydroxy-5-[[4'-methyl(1,1'-biphenyl)-4-yl]methoxy]-2-(4-morpholinyl)cyclopentyl]-5-heptenoic acid, from Intermediate 5. Purification by chromatography using 17:3 ER-methanol as eluent. I.R. ($CHBr_3$) 3500, 1735, 1710 cm⁻¹.

T.L.C. 17:3 ER-methanol Rf 0.25.

(e) [1α(Z),
2β,3β,5α]-(±)-7-[3-Hydroxy-2-(4-morpholinyl)-5-[(2-phenylthien-4-yl)methoxy]-4-heptenoic acid, compound with piperazine (2:1), m.p. 118°–119° from Intermediate 7.

Analysis Found: C, 65.5; H, 7.8; N, 5.3; $C_{27}H_{35}NO_5SA.\frac{1}{2}(C_4H_{10}N_2)$ requires: C, 5.9; H, 7.6; N, 5.3%;

(f)
[1α(Z),2β,3β,5α]-(±)-9-[5-[[(1,1'-Biphenyl)-4-yl]methoxy]-3-hydroxy-2-(4-morpholinyl)cyclopentyl]-6-nonenoic acid, from Intermediate 8. Purification by chromatography using 9:1 EA-methanol as eluent. I.R. ($CHBr_3$) 3500, 1730, 1710 cm⁻¹.

T.L.C. 9:1 EA-methanol Rf 0.26.

(g)
[1α(Z),2β,3β,5α]-(±)-7-[3-Hydroxy-2-(4-morpholinyl)-5-[(4-phenylmethyl)phenylmethoxy]cyclopentyl]-4-heptenoic acid, from the acid derived from Intermediate 9. Purification by chromatography using 9:1 ER-methanol as eluent. I.R. ($CHBr_3$) 3500, 1730, 1700 cm⁻¹.

T.L.C. 9:1 ER-methanol Rf 0.34.

(h)
[1α(Z),2β,3β,5α]-(±)-7-[3-Hydroxy-5-[[4'-methoxy(1,1'-biphenyl)-4-yl]methoxy]-2-(4-morpholinyl)cyclopentyl]-4-heptenoic acid, from Intermediate 10. Purification by chromatography using 17:3 ER-methanol as eluent. I.R ($CHBr_3$) 3500, 1730, 1710 cm⁻¹.

T.L.C. 17:3 ER-methanol Rf 0.4.

(i)
[1α(Z),2β,3β,5α]-(±)-7-[3-Hydroxy-5-[[4'-methyl(1,1'-biphenyl)-4-yl]methoxy]-2-(4-morpholinyl)cyclopentyl]-4-heptenoic acid, from Intermediate 11. Purification by chromatography using 4:1 EA-methanol as eluent. I.R. ($CHBr_3$) 3500, 3400–2300, 1730, 1710 cm⁻¹.

T.L.C. 4:1 EA-methanol Rf 0.29.

(j)
[1α(Z),2β,3β,5α]-(±)-7-[3-Hydroxy-2-(4-morpholinyl)-5-[(4-thien-2-yl)phenylmethoxy]cyclopentyl]-4-heptenoic acid, from the acid derived from Intermediate 12. Purification by chromatography using 4:1 EA-methanol as eluent.

I.R. ($CHBr_3$) 3500, 1740, 1710 cm⁻¹.
T.L.C. 3:1 EA-methanol Rf 0.28.

[1α(Z),
2β,3β,5α(E)-(±)-7-[3-Hydroxy-2-(4-morpholinyl)-5-[(3-phenyl-2-propenyl)oxy]cyclopentyl]-4-heptenoic acid, from Intermediate 13. Purification by chromatography using 9:1 through to 3:1 EA-methanol. I.R. ($CHBr_3$) 3500, 3400–2400, 1730, 1710 cm⁻¹.

T.L.C. 9:1 EA-methanol Rf 0.19.

(I)
[1α(Z),2β,3β,5α]-(±)-7-[5-[[(1,1'-Biphenyl)-4-yl]methoxy]-3-hydroxy-2-(4-thiomorpholinyl)cyclopentyl]-4-heptenoic acid, from Intermediate 14. Purification by chromatography using 17:1 EA-methanol as eluent. I.R. (CHBr₃) 3500, 1740, 1710 cm⁻¹.
T.L.C. 17:1 EA-methanol R$_f$ 0.33.

EXAMPLE 2

[1R-[1α(Z),2β,3β,5α]]-(+)-7-[5-[[(1,1'-Biphenyl)-4-yl]methoxy]-2-(4-morpholinyl)cyclopentyl]-4-heptenoic acid, A stirred solution of lithium tri-sec-butylborohydride in THF (12 ml; 1M) under nitrogen at −40° was treated slowly dropwise with a solution of Intermediate 15 (0.43 g) in dry THF (12 ml). After 0.5 h at 0° the mixture was poured into 2N H₂SO₄ (20 ml) and most of the THF was removed in vacuo. The residual aqueous solution was extracted with ER (2×20 ml) and then adjusted to pH 6.5 with pH 6.5 phosphate buffer and saturated aqueous K₂CO₃. The aqueous solution was extracted with CH₂Cl₂ (3×50 ml) and the combined extracts were dried and evaporated. The residue was purified by chromatography using 9:1 EA-methanol as eluent to give the title compound as a foam (180 mg). I.R. (CHBr₃) 3500, 1730, 1710 cm⁻¹.
T.L.C. 9:1 EA-methanol R$_f$ 0.2. $[α]_D^{21.5}$ = +68.54° D (CHCl₃).

EXAMPLE 3

(a) [1α(Z),2β,3β,5α]-( )-Methyl 7-[5-(4-Cyclohexylphenylmethoxy)-3-hydroxy-2-(4-morpholinyl)cyclopentyl]-5-heptenoate, DIBAL (8.39 ml; 1.43M) in hexane was added slowly to a stirred solution of 2,6-di-tert-butyl-4-methylphenol (5.28 g) in toluene (50 ml) under nitrogen at 4°. After 1 h, the mixture was cooled to −65° and a solution of Intermediate 2 (0.6 g) in toluene (10 ml) was added. After 4 h at −65° and 17 h at −20°, 2N HCl (35 ml) was added and stirring maintained for 1.5 h. 2N Na₂CO₃ (35 ml) and pH 6 phosphate buffer (60 ml) were added and the mixture was extracted with EA (3×80 ml). The combined extracts were dried and evaporated and the residue was purified by chromatography using 49:1 ER-methanol as eluent to give the title compound as an oil (0.48 g). I.R. (CHBr₃) 3350, 1726 cm⁻¹.
Analysis Found: C, 72.1; H, 9.2; N, 2.8; C₃₀H₄₅NO₅ requires: C, 72.1; H, 9.1; N, 2.8%.

The following compound was prepared in a similar manner:

(b) [1α(Z),2β,3β,5α]-( )-Methyl 7-[3-Hydroxy-5-[[3-methoxy(1,1'-biphenyl)-4-yl]methoxy]-2-(4-morpholinyl) cyclopentyl]-5-heptenoate, compound with ethyl acetate (5:1), from Intermediate 19. Purification by chromatography using initially EA then 19:1 EA-methanol as eluent.
I.R. (CHBr₃) 3400(br.), 1730 cm⁻¹.
Analysis Found: C, 70.7; H, 7.9; N, 2.6; C₃₁H₄₁NO₆·1/5(C₄H₈O₂) requires C, 70.6; H, 7.9; N, 2.6%.

EXAMPLE 4

(a)
[1α(Z),2β,3β,5α]-(±)-7-[5-(4-Cyclohexylphenylmethoxy)-3-hydroxy-2-(4-morpholinyl)cyclopentyl]-5-heptenoic acid A solution of the compound of Example 3a (0.39 g) in methanol (6 ml) and 2N NaOH (3 ml) was stirred at 20° for 3 h. 2N HCl (3 ml) and pH 6 phosphate buffer (50 ml) were added and the mixture was extracted with EA (3×50 ml). The combined extracts were dried and evaporated to give the title compound as a foam (0.34 g) I.R. (CHBr₃) 3500, 1730, 1710 cm⁻¹.
T.L.C. 19:1 EA-methanol R$_f$ 0.23.

The following compound was prepared in a similar manner:

(b)
[1α(Z),2β,3β,5α]-(±)-7-[3-Hydroxy-5-[[3'-methoxy(1,1'-biphenyl)-4-yl]methoxy]-2-(4-morpholinyl)cyclopentyl]-5-heptenoic acid, from the compound of Example 3b. Purification by chromatography using 17:3 ER-methanol
I.R. (CHBr₃) 3500, 1740 1710 cm⁻¹
Analysis Found: C, 70.5: H, 7.9; N, 2.4; C₃₀H₃₉NO₆ requires: C, 70.7; H, 7.7; N, 2.8%.

EXAMPLE 5

[1α(Z),2β,3β,5α]-(+)-Methyl 7-[5-[(1,1'-Biphenyl)-4-yl]methoxy]-3-hydroxy-2-(4-morpholinyl)cyclopentyl]-4-heptenoate A solution of the acid derived from the compound of Example 1a (1.2 g) in methanol (25 ml) and conc. H₂SO₄ (0.5 ml) was kept at 20° for 16 h. Water (2.5 ml) was added followed by solid NaHCO₃ until pH 8 was achieved, and the solvents were then removed in vacuo. The residue in water (20 ml) was extracted with EA (3×20 ml) and the combined extracts were dried and evaporated to give an oil (1.23 g). A portion (0.5 g) was purified by chromatography using 39:1 EA-methanol as eluent to give the title compound as an oil (0.32 g).
I.R (CHBr₃) 3500–3100, 1732 cm⁻¹.
Analysis Found: C, 72.7; H, 8.0; N, 2.7; C₃₀H₃₉NO₅ requires: C, 73.0; H, 8.0; N, 2.8%.

EXAMPLE 6

[1α(Z),2β,3β,5α]-(±)-Methyl 7-[5-[[(1,1'-Biphenyl)-[4-yl]methoxy]-3-hydroxy-2-(1-piperidinyl)cyclopentyl]-4-heptenoate DIBAL (3.6 ml; 1.43M) in hexane was added slowly to a stirred solution of 2,6-di-tert-butyl-4-methylphenol (2.29 g) in toluene (20 ml) under nitrogen at 0°. After 1 h, the mixture was cooled to −70° and a solution of Intermediate 20 (0.255 g) in toluene (8 ml) was added. After 2 h at −70° and 18 h at −20°, 2N HCl (20 ml) was added and stirring maintained for 1 h at 20°. 2N Na₂CO₃ (20 ml) and pH 6 phosphate buffer (75 ml) were added and the mixture was extracted with EA (3×40 ml). The combined extracts were dried and evaporated and the residue was purified by chromatography using 4:1 EA-methanol as eluent to give the title compound as an oil (0.117 g).
I.R. (CHBr₃) 3300(br.), 1730 cm⁻¹.
T.L.C. 4:1 EA-methanol R$_f$ 0.22.

EXAMPLE 7

[1α(Z),2β,3β,5α]-(±)-7-[5-[[(1,1'-Biphenyl)-4-yl]methoxy]-3-hydroxy-2-(1-piperidinyl)cyclopentyl]-4-heptenoic acid, compound with ethyl acetate (4:1)

A solution of the compound of Example 6 (0.096 g) in methanol (2 ml) and 2N NaOH (1 ml) was stirred at 20° for 5 h. 2N HCl (1 ml) and pH 6 phosphate buffer (30 ml) were added and the mixture was extracted with EA (3×30 ml). The combined extracts were dried and evaporated to give the title compound as a foam (0.091 g).

I.R. (CHBr$_3$) 3500–2300, 1728, 1590, 1560 cm$^{-1}$.

[M+H]$^+$: 478.2959 Calculated for C$_{30}$H$_{40}$NO$_4$: 478.2957.

EXAMPLE 8

(1α,2β,3β,5α)-(±)-7-[5-[[(1,1'-Biphenyl)-4-yl]methoxy]-3-hydroxy-2-(4-morpholinyl)cyclopentaneheptanoic acid A solution of the compound of Example 1a (0.275 g) in ethanol (15 ml) was hydrogenated over a pre-reduced suspension of 10% PdO on charcoal (1:1 with water, 0.25 g) in ethanol (10 ml) at 20° and atmospheric pressure. After 10 min, the catalyst was filtered off (hyflo) and the filtrate was evaporated to give the title compound as an oil (0.235 g).

I.R. (CHBr$_3$) 3490, 1735, 1705 cm$^{-1}$.

T.L.C. AgNO$_3$ impregnated SiO$_2$ 4:1 EA-methanol R$_f$ 0.5.

EXAMPLE 9

[1R-1α(Z),2β,3β,5α]-(+)-Methyl 7-[5[[1,1'-Biphenyl)-4-yl]methoxy]-3-hydroxy-2-(1-piperidinyl)cyclopentyl]-4-heptenoate To a stirred solution of potassium t-butoxide (2.05 g) in THF (80 ml) was added (3-carboxypropyl)triphenylphosphonium bromide (3.9 g). After 0.5 h at 20° a solution of Intermediate 34 (0.463 g) in THF (10 ml) was added and stirring continued at 20° for 0.75 h. Water (2 ml) was added and the solvent removed in vacuo. The residue was taken into water (100 ml), basified to pH 14 with 2N NaOH and washed with ER (3×60 ml). The aqueous solution was adjusted to pH 6.5 with 2N HCl and extracted with CH$_2$Cl$_2$ (3×50 ml). The combined extracts were concentrated, re-dissolved in 1:1 EA-CH$_2$Cl$_2$ (15 ml) and then treated with an excess of an ethereal solution of diazomethane. Excess diazomethane was destroyed with acetic acid and the solution then diluted with EA (30 ml) and washed with 2N Na$_2$CO$_3$ (40 ml). The organic solution was dried and evaporated and the residue purified by chromatography using 4:1 EA-methanol an eluent to give the title compound as an oil (0.428 g). [α]$_D^{23}$ = +60.10° (CHCl$_3$)

IR (Neat) 3600–3100(br.), 1735 cm$^{-1}$.

T.L.C. 65:35 EA-methanol R$_f$ 0.22.

EXAMPLE 10

[1R-[1α(Z),2β,3β,5α]-(+)-7-[5-[[(1,1'-Biphenyl)-4-yl]methoxy]-3-hydroxy-2-(1-piperidinyl)cyclopentyl]-4-heptenoic acid, compound with ethyl acetate (2.1:1)

5N NaOH (1.5 ml) was added to the compound of Example 9 (0.385 g) in methanol (3 ml) and the mixture stirred vigorously at 30°–40° for 3h. Water (50 ml) was added and the mixture extracted with ER (3×20 ml). The aqueous solution was adjusted to pH 6 with 2N HCl and pH 6 phosphate buffer solution (20 ml) and then extracted with EA (3×30 ml). The combined extracts were dried and concentrated to give the title compound as a foam (0.283 g).

[α]$_D^{26}$ = +60.49° (CHCl$_3$).

IR (CHBr$_3$) 3400–2220(br.), 1724 cm$^{-1}$.

T.L.C. 25:15:8:2 EA-iPrOH-H$_2$O-NH$_4$OH R$_f$ 0.34.

EXAMPLE 11

[1α(Z),2β,3β,5α]-(±)-7-[3-Hydroxy-5-[[4'-methoxy(1,1'-biphenyl)-4-yl]methoxy]-2-(1-piperidinyl)cyclopentyl]-4-heptenoic acid, compound with ethyl acetate and dichloromethane (20:3:2)

(3-Carboxypropyl)triphenylphosphonium bromide (1.55 g) was added under nitrogen to a stirred solution of potassium t-butoxide (0.775 g) in dry THF (25 ml). After 40 min a solution of Intermediate 41 (0.43 g) in THF (7 ml) was added and the mixture stirred for 35 min. at room temperature. Water (80 ml) followed by 2N NaOH (5 ml) were added and the mixture extracted with ER (2×100 ml). The aqueous solution was neutralised with 2N H$_2$SO$_4$, treated with pH 6.5 phosphate buffer (10%, 25 ml) and extracted with EA (2×70 ml). The combined extracts were washed with phosphate buffer (3×50 ml), dried (Na$_2$SO$_4$) and evaporated in vacuo to give the title compound as a foam (0.3 g).

IR (CHBr$_3$) 3200–2300(br.), 1720(br.)cm$^{-1}$.

T.L.C. 25:15:8:2 EA-iPrOH-H$_2$O-NH$_4$OH R$_f$ 0.43.

EXAMPLE 12

[1R-[1α(Z),2β,3β,5α]-(+)-7-5-[[(1,1'-Biphenyl)-4-yl]methoxy]-3-hydroxy-2-(1-piperidinyl)cyclopentyl]-4-heptenoic acid, hydrochloride The product of Example 9 (10.38 g) was stirred with 74 OP ethanol (60 ml) and 5N NaOH (30 ml) at 20° for 16 h. The solution was diluted with water (400 ml) and then extracted with ER (2×150 ml). The aqueous phase was adjusted to pH 6 with 2N HCl and extracted with CH$_2$Cl$_2$ (3×200 ml). Evaporation of the combined extracts gave a foam (9.45 g), the majority (9.3 g) of which was taken up into CH$_2$Cl$_2$ (50 ml) and treated with an excess of an ethereal solution of hydrogen chloride. Evaporation in vacuo and trituration of the residue with ER (4×75 ml) gave the title compound as a powder (9.28 g). Crystallisation of a sample from EA-methanol gave material of m.p. 124°–126°.

[α]$_D^{25}$ = +63.1° (CHCl$_3$).

Pharmaceutical Examples

Tablets

These may be prepared by direct compression or wet granulation. The direct compression method is preferred but may not be suitable in all cases as it is dependent upon the dose level and physical characteristics of the active ingredient.

| A. Direct Compression | mg/table |
| --- | --- |
| Active ingredient | 100.00 |
| Microcrystalline Cellulose B.P.C. | 298.00 |
| Magnesium Stearate | 2.00 |
| Compression Weight | 400.00 mg |

The active ingredient is sieved through a 250 m$^{-6}$ sieve, blended with the excipients and compressed using 10.0 mm punches. Tablets of other strengths may be prepared by altering the compression weight and using punches to suit.

| B. Wet Granulation | mg/tablet |
|---|---|
| Active ingredient | 100.00 |
| Lactose B.P. | 238.00 |
| Starch B.P. | 40.00 |
| Pregelatinised Maize Starch B.P. | 20.00 |
| Magnesium Stearate B.P. | 2.00 |
| Compressed Weight | 400.00 mg |

The active ingredient is sieved through a 250 $m^{-6}$ sieve and blended with the lactose, starch and pregelatinised starch. The mixed powders are moistened with purified water, granules are made, dried, screened and blended with the magnesium stearate. The lubricated granules are compressed into tablets as described for the direct compression formulae. The tablets may be film coated with suitable film forming materials, e.g. methyl cellulose or hydroxylpropyl methyl cellulose using standard techniques. Alternatively the tablets may be sugar coated.

| Capsules | mg/capsule |
|---|---|
| Active ingredient | 100.00 |
| *STA-RX 1500 | 99.00 |
| Magnesium Stearate B.P. | 1.00 |
| Fill Weight | 200.00 mg |

*A form of directly compressible starch supplied by Colorcorn Ltd., Orpington, Kent.

The active ingredient is sieved through a 250 $m^{-6}$ sieve and blended with the other materials. The mix is filled into No. 2 hard gelatin capsules using a suitable filling machine. Other doses may be prepared by altering the fill weight and if necessary changing the capsule size to suit.

| Inhalation Cartridges | /cartridge |
|---|---|
| Active ingredient (micronised) | 3 mg |
| Lactose B.P. to | 25 mg |

The active ingredient is micronised so that the majority of the particles are between 1 $m^{-6}$ and 5 $m^{-6}$ m in longest dimensions and none are greater than 10 $m^{-6}$. The active ingredient is then blended with the lactose and the mix is filled into No. 3 hard gelatin capsules using a suitable filling machine.

| Suspensions | mg/5 ml dose |
|---|---|
| Active ingredient | 100.00 |
| Aluminum monostearate | 75.0 |
| Sucrose (powdered) | 125.0 |
| Flavour | as required |
| Color | |
| Fractionated coconut oil to | 5.00 ml. |

The aluminium monostearate is dispersed in about 90% of the fractionated coconut oil. The resulting suspension is heated to 115° C. while stirring and then cooled. The flavour and colour are added and the active ingredient and sucrose are suitably dispersed The suspension is made up to volume with the remaining fractionated coconut oil and mixed.

| Injection for Intravenous Administration | |
|---|---|
| Active ingredient | 50 mg |
| Suitable vehicle to | 5 ml. |

A sterile presentation of the active ingredient in an ampoule or vial together with an ampoule containing a suitable vehicle. The former may be prepared by (a) filling sterile material into vials under aseptic conditions (b) freeze drying a sterile solution of the active ingredient under aseptic conditions.

The vehicle may be (a) Water for Injections B.P. (b) Water for Injections B.P. containing: (1) sodium chloride to adjust the tonicity of the solution and/or (2) buffer salts or dilute acid or alkali to facilitate solution of the active ingredient.

The vehicle is prepared, clarified and filled into appropriate sized ampoules sealed by fusion of the glass. The vehicle is sterilised by heating in an autoclave using one of the acceptable cycles.

What is claimed is:

1. Compounds of the general formula (I)

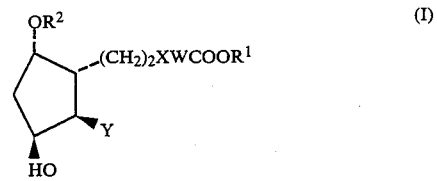

wherein
 R$^1$ is a hydrogen atom or a C$_{1-6}$alkyl group;
 W is a straight or branched C$_{1-7}$ alkylene group;
 X is cis or trans —CH=CH—;
 Y is a saturated heterocyclic amino group (attached to the cyclopentane ring via the nitrogen atom) selected from piperidino, morpholino and thiamorpholino; and R$^2$ is a phenylalkyl group in which the alkyl portion contains 1-3 carbon atoms and the phenyl is substituted by phenyl (C$_{1-3}$) alkyl, phenyl, or (C$_{1-3}$) alkoxyphenyl, and the physiologically acceptable salts and solvates thereof.

2. Compounds as claimed in claim 1 in which R$^1$ is a hydrogen atom.

3. Compounds as claimed in claim 1 in which X is cis —CH=CH— and W is —CH$_2$CH$_2$—.

4. Compounds as claimed in claim 1 in which:
 R$^1$ is a hydrogen atom,
 W is —CH$_2$CH$_2$—,
 X is cis —CH=CH—,
 Y is morpholino or piperidino, and
 R$^2$ is benzyl in which the phenyl group is substituted by phenyl or methoxyphenyl, and the physiologically acceptable salts and solvents thereof.

5. [1α(z),2β,3β,5α]-(±)-7-[5[[(1,1'-biphenyl)-4-yl]methoxy]-3-hydroxy-2-(1-piperidinyl)cyclopentyl]-4-heptenoic acid and the physiolgically acceptable salts and solvates thereof.

6. The 1R-isomer of the compound as claimed in claim 5.

7. A pharmaceutical composition comprising an antithrombotic effective amount of a compound as claimed in claim 1 together with one or more pharmaceutical carriers.

8. A composition as claimed in claim 7 wherein said compound is [1α(Z),2β,3β,5α]-(±)-7-(5-[[(1,1'-biphenyl)-4-yl]methoxy]-3-hydroxy-2-(1-piperidinyl)-cyclopentyl]-4-heptenoic acid and the physiologically acceptable salts and solvates thereof.

9. A composition as claimed in claim 7 wherein said compound is [1R-[1α(Z),2β,3β,5α]]-(+)-7-[5-[[(1,1'-biphenyl)-4-yl]methoxy]-3-hydroxy-2-(1-piperidinyl)-cyclopentyl]-4-heptenoic acid, hydrochloride.

10. A composition as claimed in claim 7 in the form of a tablet or capsule.

11. A method for the treatment or prevention of occlusive vascular diseases which comprises administering to the patient an effective amount of a compound as claimed in claim 1 or a physiologically acceptable salt or solvate thereof.

12. A method as claimed in claim 11 wherein said compound is [1α(Z),2β,3β,5α]-(±)-7-[5-[[(1,1'-biphenyl)-4-yl]methoxy]-3-hydroxy-2-(1-piperidinyl)-cyclopentyl]-4-heptenoic acid and the physiologically acceptable salts and solvates thereof.

13. A method as claimed in claim 12 wherein said compound is [1R-[1α(Z), 2β,3β,5α]]-(+)-7-[[(1,1'-biphenyl)-4-yl]methoxy]-3-hydroxy-2-(1-piperidinyl)-cyclopentyl]-4-heptenoic acid, hydrochloride.

* * * * *